(12) United States Patent
Mijers

(10) Patent No.: US 12,178,783 B2
(45) Date of Patent: Dec. 31, 2024

(54) ANTI-FREE-FLOW VALVE ASSEMBLY WITH FLOW BYPASS

(71) Applicant: Illinois Tool Works Inc., Glenview, IL (US)

(72) Inventor: Jan Willem Marinus Mijers, Heemstede (NE)

(73) Assignee: ILLINOIS TOOL WORKS INC., Glenview, IL (US)

( * ) Notice: Subject to any disclaimer, the term of this patent is extended or adjusted under 35 U.S.C. 154(b) by 934 days.

(21) Appl. No.: 17/228,389

(22) Filed: Apr. 12, 2021

(65) Prior Publication Data

US 2021/0315779 A1  Oct. 14, 2021

Related U.S. Application Data

(60) Provisional application No. 63/009,804, filed on Apr. 14, 2020.

(51) Int. Cl.
*A61M 39/22* (2006.01)
*A61J 15/00* (2006.01)

(52) U.S. Cl.
CPC ........ *A61J 15/0092* (2013.01); *A61M 39/225* (2013.01)

(58) Field of Classification Search
CPC .................................. A61M 39/225
See application file for complete search history.

(56) References Cited

U.S. PATENT DOCUMENTS

| | | |
|---|---|---|
| 4,279,401 A | 7/1981 | Ramirez et al. |
| 5,147,333 A | 9/1992 | Raines |
| 5,297,777 A | 3/1994 | Yie |
| 5,740,810 A | 4/1998 | Johnson et al. |
| 6,117,102 A | 9/2000 | Schwartz et al. |
| 2007/0272311 A1* | 11/2007 | Trocki ................ A61M 39/223 137/601.2 |
| 2015/0265784 A1 | 9/2015 | Lampert et al. |

OTHER PUBLICATIONS

CME Medical "MicroSet/BodySet instructions for use administration set with male luer-lock to be used only with BodyGuardTM Infusion Pumps" (2 Pages).
International Preliminary Report on Patentability received for related PCT App. No. PCT/US2021/027118 dated Oct. 27, 2022 (11 pages).

* cited by examiner

*Primary Examiner* — Courtney B Fredrickson
(74) *Attorney, Agent, or Firm* — The Small Patent Law Group LLC; Christopher R. Carroll

(57) ABSTRACT

An enteral feeding valve assembly includes a housing assembly that is fluidly coupled with an upstream line and a downstream line. A diverging conduit inwardly extends from an inlet and a primary conduit inwardly extends from an outlet of the housing. The diverging conduit splits into a bypass conduit and a flow-through conduit. The flow-through conduit is fluidly coupled with the primary conduit by a check valve. A plunger valve includes one or more plunger conduits and moves in a first direction to fluidly couple the inlet with the primary conduit and the outlet via the bypass conduit and the one or more plunger conduits. The plunger valve moves in a second direction to de-couple the inlet from the primary conduit and the outlet via the bypass conduit and the one or more plunger conduits. The flow-through conduit directs the fluid to the outlet through the check valve.

18 Claims, 5 Drawing Sheets

ANTI-FREE-FLOW VALVE ASSEMBLY WITH FLOW BYPASS

CROSS-REFERENCE TO RELATED APPLICATIONS

This application claims priority to U.S. Provisional Application No. 63/009,804, which was filed on 14 Apr. 2020, and the entire subject matter of which is incorporated herein by reference.

BACKGROUND

Technical Field

The subject matter described herein relates to valves, such as valves used to control the flow of fluids for enteral feeding.

Discussion of Art

Valves can be used to control the flow of fluids. For example, check valves can control the direction in which a gas or liquid flows by preventing flow in one or more directions while allowing flow in one or more other directions. As another example, valves can restrict the rate at which the gas or liquid flows through the valves.

Valves are used in enteral feeding to control the direction and/or rate at which nutritional liquid is delivered to the gastrointestinal (GI) tract of patients. These valves can be placed between a supply line (e.g., a tube that directs the nutritional liquid from a source to the valve) and a patient line (e.g., a tube that is connected with the GI tract of the patient). The valve can include a check valve that prevents back flow of fluid from the patient line to the supply line. This valve also can restrict how rapidly the fluid flows from the supply line to the patient line to prevent too much fluid from being delivered to the patient too quickly.

But, use of some of these known valves can take a considerable amount of time to initially fill the patient line with the nutritional fluid. The valves can only permit a slow passage of the fluid from the supply line to the patient line. As a result, the caregiver who is filling the patient line with the nutritional fluid may need to wait and watch the patient line slowly fill with the nutritional fluid. This can take several minutes, which is time that may be better spent administering other care to the patient and/or other patients.

BRIEF DESCRIPTION

In one embodiment, an enteral feeding valve assembly is provided. The valve assembly includes a housing assembly having an inlet configured to be fluidly coupled with an upstream line and an outlet configured to be fluidly coupled with a downstream line. The housing assembly includes a diverging conduit that extends inward from the inlet and a primary conduit that extends inward from the outlet. The diverging conduit splits into a bypass conduit and a flow-through conduit. The flow-through conduit is fluidly coupled with the primary conduit by a check valve. The valve assembly also includes a plunger valve disposed in the housing assembly and configured to move relative to the housing assembly. The plunger valve includes one or more plunger conduits. The plunger valve is configured to be actuated to move in a first direction in the housing assembly to fluidly couple the inlet of the housing assembly with the primary conduit and the outlet of the housing assembly via the bypass conduit of the housing assembly and the one or more plunger conduits of the plunger valve. The plunger valve directs fluid received via the inlet of the housing assembly to the outlet and around the check valve in the housing assembly while the plunger valve is actuated. The plunger valve is configured to move in a different, second direction upon release of the plunger valve to de-couple the inlet of the housing assembly with the primary conduit and the outlet via the bypass conduit of the housing assembly and the one or more plunger conduits of the plunger valve. The flow-through conduit of the housing assembly directs the fluid received via the inlet of the housing assembly to the outlet through the check valve in the housing assembly while the plunger valve is released.

In one embodiment, a valve assembly is provided that includes a cap plate having an inlet configured to be fluidly coupled with an upstream line. The cap plate includes a diverging conduit that extends inward from the inlet and that splits into a bypass conduit and a flow-through conduit. The valve assembly also includes a rigid housing having an outlet configured to be fluidly coupled with a downstream line. The housing includes a primary conduit that extends inward from the outlet. The primary conduit is fluidly coupled with the flow-through conduit by a check valve. The valve assembly also includes a flexible plunger valve disposed in the housing and configured to move relative to the housing. The plunger valve includes one or more plunger conduits and is configured to be actuated to move in a first direction in the housing to fluidly couple the inlet of the cap plate with the primary conduit and the outlet of the housing via the bypass conduit of the cap plate and the one or more plunger conduits of the plunger valve. The plunger valve directs fluid received via the inlet of the cap plate to the outlet of the housing and around the check valve in the housing assembly while the plunger valve is actuated.

In one embodiment, a method is provided that includes filling an upstream line coupled with an inlet of an enteral feeding valve assembly with a fluid, and pressing a plunger valve in the valve assembly downward into a housing assembly of the valve assembly. The plunger valve is pressed downward to establish a bypass fluid flow path for the fluid to flow around a check valve in the valve assembly. The method also includes priming a downstream line coupled with an outlet of the valve assembly with the fluid that flows through the bypass fluid flow path and around the check valve in the valve assembly, and releasing the plunger valve to interrupt the bypass fluid flow path and to direct the fluid to flow through the check valve in the valve assembly to the downstream line.

BRIEF DESCRIPTION OF THE DRAWINGS

The inventive subject matter may be understood from reading the following description of non-limiting embodiments, with reference to the attached drawings, wherein below.

DETAILED DESCRIPTION

Figure 1:
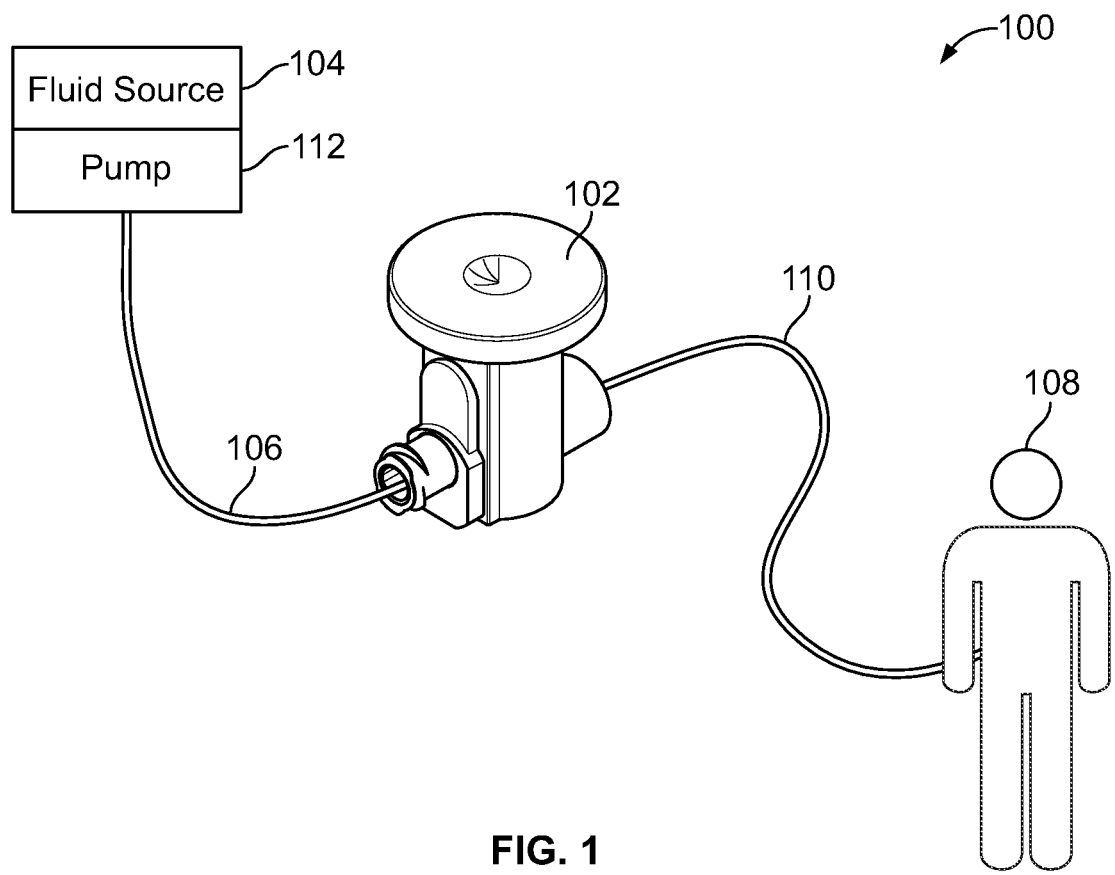
FIG. 1 schematically illustrates one example of an enteral feeding system.

One or more embodiments of the inventive subject matter described herein provide valve assemblies and associated methods that enable faster priming of patient lines in enteral feeding systems. FIG. 1 schematically illustrates one example of an enteral feeding system 100. The system 100 includes an anti-free-flow bypass valve assembly 102 that is configured to be fluidly coupled with a fluid source 104 of a fluid by one or more supply lines 106 and with a patient 108 by one or more patient lines 110. The components and objects shown in FIG. 1 are not drawn to scale. The source 104 may be a bag or other container of the fluid, such as a nutritional fluid that is supplied to the GI tract of the patient 108. A pump 112, such as an infusion pump, may be connected with the source 104 and the supply line 106 to force the fluid in the source 104 toward the patient 108 via the supply line 106 and the patient line 110. Alternatively, the pump 112 may not be used but gravity may be used to force the fluid through the lines 106, 110. The lines 106, 110 represent conduits, such as tubes. The lines 106, 110 optionally can be referred to an upstream or distal line 106 and a downstream or proximal line 110, respectively. While the description herein focuses on use of the valve assembly 102 with enteral feeding, not all embodiments of the inventive subject matter are limited or otherwise restricted to enteral feeding. At least one embodiment of the valve assembly 102 may be used with other applications that seek to control how quickly a fluid is directed from one line (e.g., the line 106) to another line (e.g., the line 110).

The valve assembly 102 can be used to control how quickly the fluid from the source 104 passes from the upstream line 106, through the valve assembly 102, and fills the downstream line 110, such as during priming of the downstream line 110 (e.g., the initial filling of the downstream line 110). As described herein, gravity and/or the pump 112 can force the fluid from the fluid source 104 to the valve assembly 102 via the upstream line 106. In one mode or state of the valve assembly 102 (e.g., the default or non-actuated mode or state), the fluid may pass through a check valve that allows fluid flow from the fluid source 104 or upstream line 106 toward the patient 108 or downstream line 110, but not from the patient 108 or downstream line 110 toward the fluid source 104 or upstream line 106. This check valve also can restrict how rapidly the fluid can flow through the valve assembly 102 from the upstream line 106 to the downstream line 110. To speed up the filling of the downstream line 110 with the fluid, the state or mode of the valve assembly 102 can be changed (e.g., to a bypass or actuated mode or state). In this mode or state, the path in which the fluid flow in the valve assembly 102 changes so that the fluid no longer passes through the check valve in the valve assembly 102. The fluid may more rapidly flow from the upstream line 106 to the downstream line 110 as flow of the fluid is not restricted by the check valve and/or the smaller flow paths available to the fluid in the default or non-actuated state of the valve assembly 102. Once the downstream line 110 is filled or filled to an extent desired by an operator of the valve assembly 102, the valve assembly 102 may be switched to the default or non-actuated mode or state so that the fluid in the upstream line 106 must again pass through the check valve within the valve assembly 102 to reach the downstream line 110.

The valve assembly 102 can solve the problem with priming of the downstream line 110 taking too long by allowing an operator to actuate the valve assembly 102 to the bypass state and to more rapidly fill and prime the downstream line 110 with the fluid. Once the filling or priming is complete, the valve assembly 102 can return to the default or non-actuated state, where the fluid passes much more slowly from the upstream line 106 to the downstream line 110.

In one embodiment, while in the default or non-actuated state, the valve assembly 102 only allows the fluid to move through the valve assembly 102 from the upstream line 106 to the downstream line 110 in only a single direction (toward the patient) and at a rate or speed that is safe for the GI tract of the patient 108 (e.g., a speed or rate that is no faster than a designated threshold, such as no faster than twenty-five milliliters per hour (mL/h) or no faster than fifty mL/h). While in the bypass or actuated state, the valve assembly 102 allows the fluid to move through the valve assembly 102 in either direction (e.g., toward or away from the patient 108) and at a rate or speed that is not safe for the GI tract of the patient 108 (e.g., a speed or rate that is faster than the designated threshold).

Figure 2:
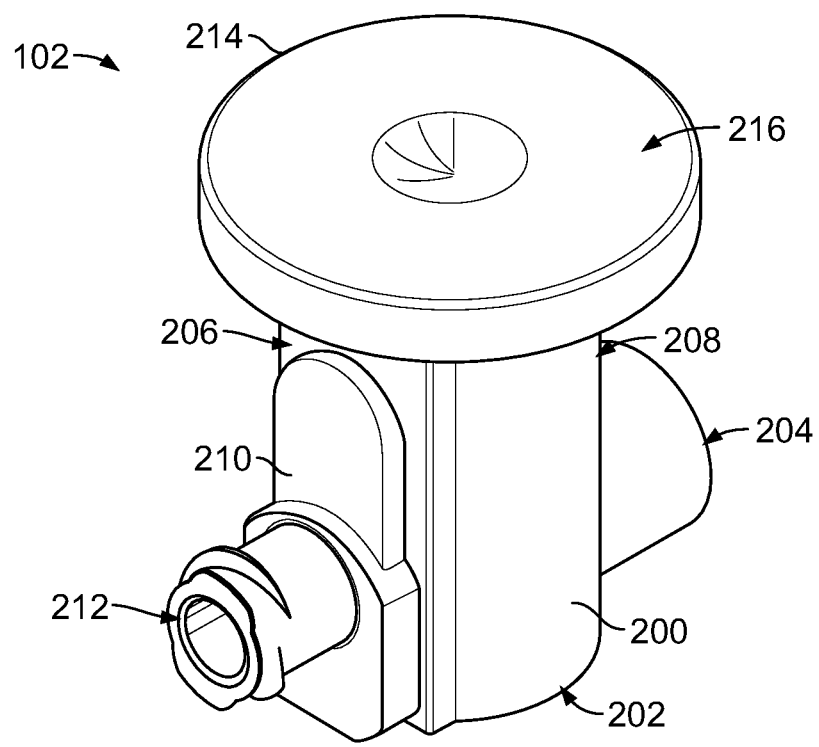
FIG. 2 illustrates one example of a perspective view of a valve assembly shown in FIG. 1.
Figure 3:
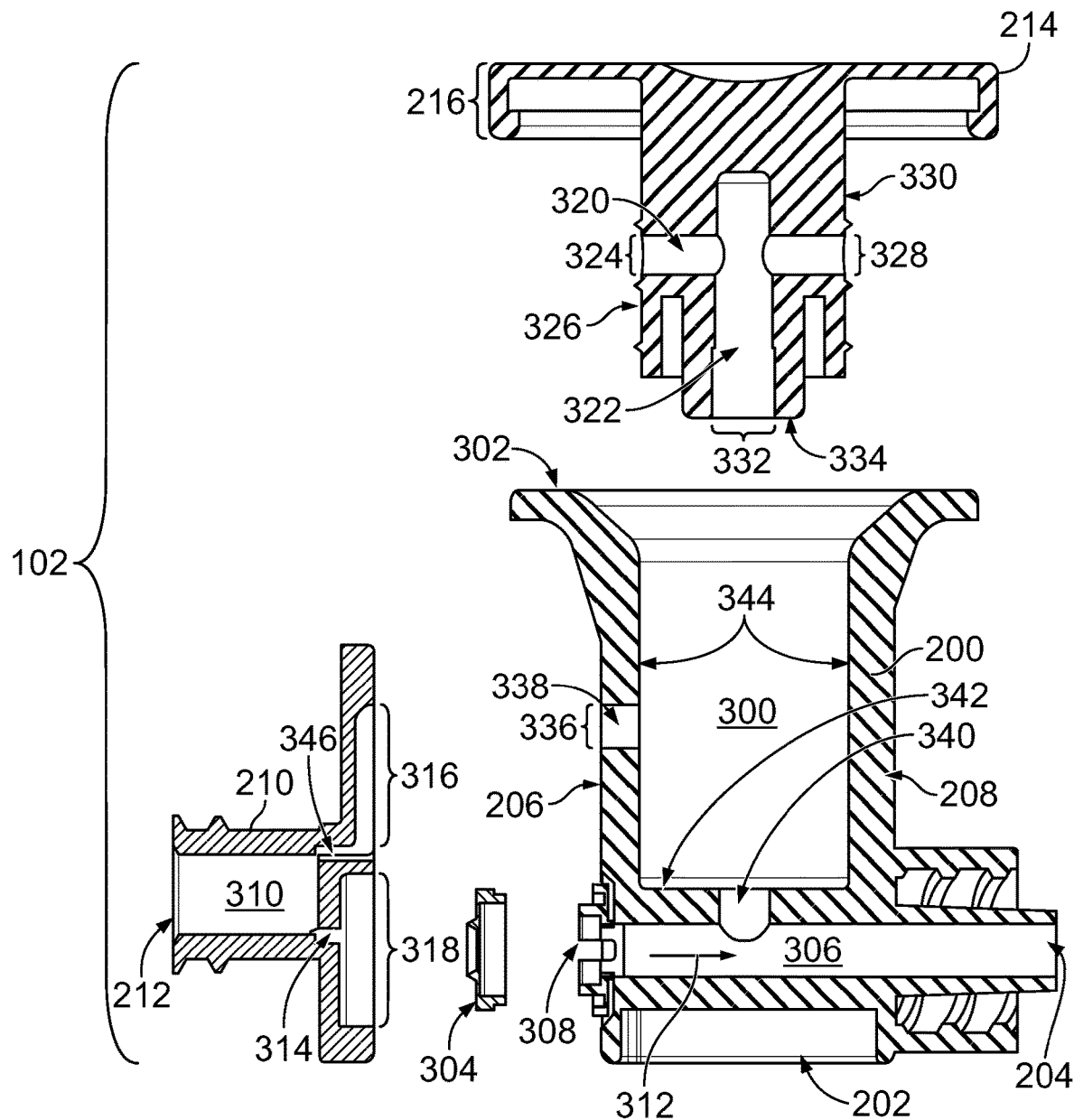
FIG. 3 illustrates one example of an exploded view of the valve assembly shown in FIG. 2.

FIG. 2 illustrates one example of a perspective view of the valve assembly 102 shown in FIG. 1. FIG. 3 illustrates one example of an exploded view of the valve assembly 102 shown in FIG. 2. The valve assembly 102 includes an outer housing 200 having an interior chamber 300 (shown in FIG. 3) that is open at an upper or actuation end 302 (shown in FIG. 3) of the housing 200. A bottom or opposite end 202 of the housing 200 is closed, as shown in FIG. 3. The housing 200 includes a primary flow conduit 306 closer to the bottom end 202 than the upper end 302 of the housing 200. As described below, the fluid from the fluid source 104 (shown in FIG. 1) flows through the entire length of the primary flow conduit 306 in the housing 200 while the valve assembly 102 is in the default or non-actuated state. The fluid flows through only part, and less than the entire length, of the primary flow conduit 306 while the valve assembly 102 is in the bypass or actuated state.

The housing 200 has a primary conduit inlet 308 on an inlet side 206 of the housing 200 and a primary conduit outlet 204 on an opposite outlet side 208 of the housing 200. As shown, the housing 200 is elongated from the upper end 302 to the bottom end 202 with the sides 206, 208 extending from the upper end 302 to the bottom end 202. The primary flow conduit 306 extends from the primary conduit inlet 308 to the primary conduit outlet 204.

A check valve 304 (shown in FIG. 3) may be coupled with the housing 200 at the primary conduit inlet 308. For example, the check valve 304 may be press-fit, snap-fit, adhered to, welded to, or otherwise secured to the housing 200 at the primary conduit inlet 308 such that the fluid passing through the check valve 304 exits the check valve 304 into the primary flow conduit 306. As described herein, the check valve 304 may be positioned at the primary conduit inlet 308 such that the fluid entering the valve assembly 102 through the check valve 304 can only move through the primary flow conduit 306 in a lateral direction 312 that is oriented from the inlet side 206 toward the outlet side 208.

A cap plate 210 optionally may be coupled with the inlet side 206 of the housing 200. The cap plate 210 includes an internal diverging conduit 310 (shown in FIG. 3) that extends from a housing inlet 212 to a bypass conduit 346

(shown in FIG. 3) and a flow-through conduit 314 (shown in FIG. 3). For example, the diverging conduit 310 may bifurcate into different branches with one branch being the bypass conduit 346 and the other branch being the flow-through conduit 314. Optionally, the diverging conduit 310 may split into more than two different branches. The conduits 310, 346, 314 are fluidly coupled with each other, as shown in FIG. 3.

While the cap plate 210 is shown as a separate component to the housing 200, alternatively, the cap plate 210 and the housing 200 may be a single body. A combination of the cap plate 210 and the housing 200 (whether the cap plate 210 and housing 200 are separate or a unitary body) can be referred to as a housing assembly.

The bypass conduit 346 extends from the diverging conduit 310 to a bypass outlet 316 of the cap plate 210. The flow-through conduit 314 extends from the diverging conduit 310 to a flow-through outlet 318 of the cap plate 210. As shown in FIG. 3, the conduits 346, 314 are separate from each other and the outlets 316, 318 are separate from each other such that fluid flowing in the bypass conduit 346 exits the cap plate 210 via the bypass outlet 316 and not the flow-through outlet 318 and fluid flowing in the flow-through conduit 314 exits the cap plate 210 via the flow-through outlet 318 and not the bypass outlet 316. Fluid flowing in the diverging conduit 310 may flow into either the conduits 346, 314 depending on the state or mode of the valve assembly 102, as described herein. Optionally, the conduits 310, 346, 314, inlet 212, and outlets 316, 318 may be formed inside the housing 200 and the cap plate 210 may be omitted from the valve assembly 102.

The valve assembly 102 includes a plunger valve 214 that is partially disposed within the open-ended interior chamber 300 of the valve housing 200. The plunger valve 214 moves within the interior chamber 300 to control the flow path of fluid through the valve assembly 102 as described herein. The plunger valve 214 includes a contact head or button 216 that is engaged by a user to depress the plunger valve 214 into the interior chamber 300 of the valve housing 200. In the illustrated embodiment, the contact head 216 is a disc-shaped body having an indentation or recess formed therein. Alternatively, the contact head 216 may have another shape and/or may not have the indentation or recess.

The plunger valve 214 includes intersecting lateral and vertical plunger conduits 320, 322 (shown in FIG. 3). These conduits 320, 322 intersect each other in the body of the plunger valve 214 such that fluid flowing in the lateral conduit 320 flows into the vertical conduit 322. In the illustrated embodiment, the lateral conduit 320 extends from a first lateral inlet 324 formed in a first side 326 of the body of the plunger valve 214 to an opposite second lateral inlet 328 formed in an opposite second side 330 of the body of the plunger valve 214. Stated differently, the lateral conduit 320 extends through the entirety of the width of the plunger valve 214 from the external side 326 to the opposite external side 330. This can allow for the plunger valve 214 to be inserted into the interior chamber 300 of the valve housing 200 with either inlet 324 or 328 facing the side 206 of the housing 200, the cap plate 210, and/or the bypass outlet 316. Alternatively, the lateral conduit 320 may extend only from the lateral inlet 324 in the first side 326 of the body of the plunger valve 214 to the vertical conduit 322 (and not extend to the second side 330). The vertical conduit 322 is fluidly coupled with the lateral conduit 320 by intersecting the lateral conduit 320 and extends to a plunger outlet 332 on a bottom side 334 of the body of the plunger valve 214.

The valve housing 200 includes a bypass inlet 336 on or in the side 206 of the valve housing 200. The bypass inlet 336 is fluidly coupled with a lateral bypass conduit 338 in the valve housing 200. The lateral bypass conduit 338 fluidly couples the bypass inlet 336 with the interior chamber 300, as shown in FIG. 3. The valve housing 200 also includes a vertical bypass conduit 340 that is fluidly coupled with the interior chamber 300. The vertical bypass conduit 340 extends from the interior chamber 300 to the primary flow conduit 306. For example, the valve housing 200 includes a bottom interior surface 342 of the interior chamber 300 and vertical interior surfaces 344 of the interior chamber 300. The lateral bypass conduit 338 extends from the side 206 of the valve housing 200 to the vertical interior surface 344 and the vertical bypass conduit 340 extends from the bottom interior surface 342 of the interior chamber 300 to the primary flow conduit 306.

Figure 4:
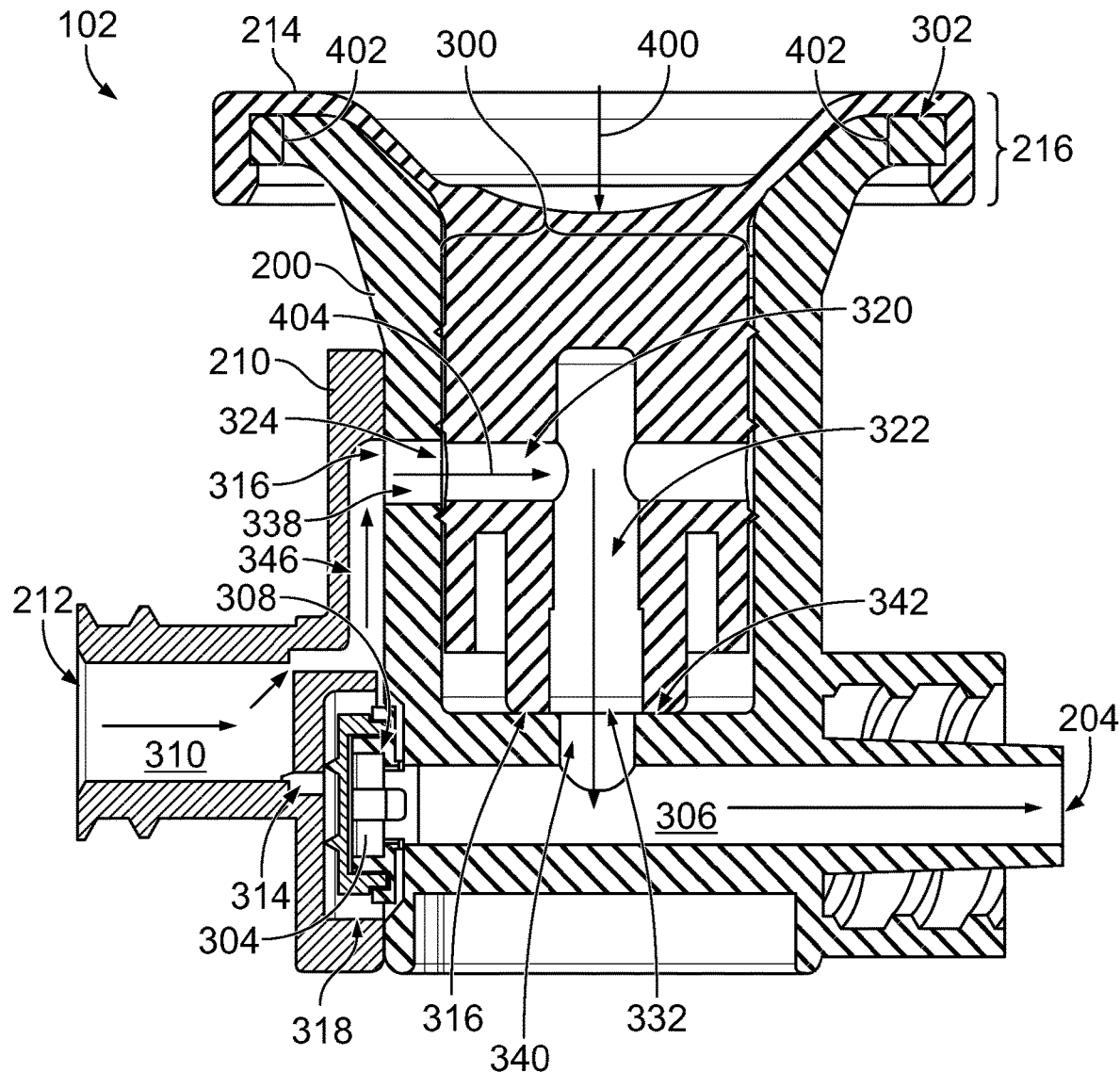
FIG. 4 illustrates one example of operation of the valve assembly in the bypass or actuated state of the valve assembly.
Figure 5:
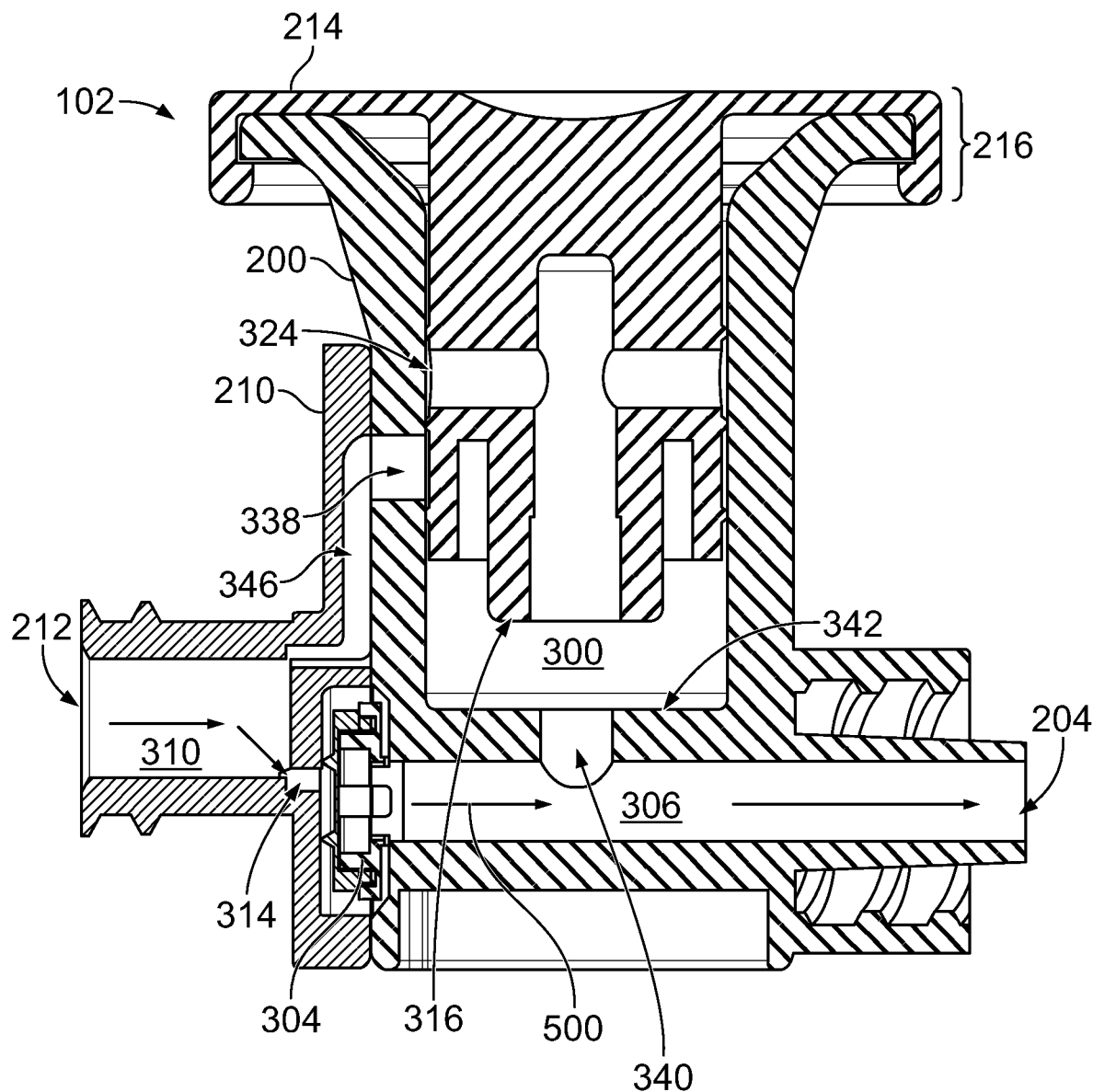
FIG. 5 illustrates one example of operation of the valve assembly in the default or non-actuated state of the valve assembly.

With continued reference to FIGS. 2 and 3, FIGS. 4 and 5 illustrate examples of operation of the valve assembly 102. FIG. 4 illustrates one example of operation of the valve assembly 102 in the bypass or actuated state of the valve assembly 102. FIG. 5 illustrates one example of operation of the valve assembly in the default or non-actuated state of the valve assembly 102. One end of the upstream line 106 (shown in FIG. 1) is coupled with the fluid source 104 (shown in FIG. 1) directly or indirectly (e.g., via one or more other lines and/or the pump 112). Another end of the upstream line 106 is coupled with the cap inlet 212 of the cap plate 210. One end of the downstream line 110 (shown in FIG. 1) is coupled with the primary conduit outlet 204 of the valve assembly 102. Another end of the downstream line 110 may not yet be coupled with the patient 108 (shown in FIG. 1) until the downstream line 110 is filled or otherwise primed.

During initial filling of the downstream line 110 with the fluid from the fluid source 104, an operator or user of the valve assembly 102 may press the contact head 216 of the plunger valve 214 along an actuation direction 400 into the interior chamber 300 of the valve housing 200. The plunger valve 214 may be formed from a flexible body while the valve housing 200 is formed from a rigid body. For example, the plunger valve 214 may be made from a material (e.g., silicone rubber) that is more flexible than the valve housing 200 when subjected to equivalent forces. The valve housing 200 can be formed from a rigid thermoplastic or other polymer, one or more metals, or the like.

As shown, the end 302 of the valve housing 200 laterally protrudes and sits within recesses 402 of the contact head 216 of the plunger valve 214. As the plunger valve 214 is pressed downward into the interior chamber 300, the contact head 216 may flex as shown in FIG. 4. The downward movement of the plunger valve 214 causes the lateral inlet 324 of the plunger valve 214 to line up with and establish fluid communication with the lateral bypass conduit 338 of the valve housing 200, which is lined up with and fluidly coupled with the bypass outlet 316 of the cap plate 210. Additionally, the downward movement of the plunger valve 214 can cause the bottom side 334 of the plunger valve 214 to engage or directly abut (e.g., without any intervening components) the bottom interior surface 342 of the interior chamber 300 in the valve housing 200. The downward movement and engagement of the bottom side 316 of the plunger valve 214 with the bottom interior surface 342 of the interior chamber 300 also causes the plunger outlet 332 to line up with and establish fluid communication with the vertical bypass conduit 340.

Fluid flows from the supply line 106 into the cap inlet 212 of the cap plate 210 (e.g., due to gravity, force generated by the pump 112, and/or manually generated force). The fluid flows into the diverging conduit 310 and can flow into the flow-through conduit 314 and/or the bypass conduit 346. As shown in FIG. 4, the check valve 304 is located within the flow-through outlet 318 of the cap plate 210 such that the check valve 304 is disposed along the flow path from the outlet 318 to the inlet 308 of the primary flow conduit 306. Alternatively, the check valve 304 may not be located in the outlet 318 but may be otherwise located between the outlet 318 and the inlet 308.

The check valve 304 may resist flow of the fluid more than the bypass conduit 346. This can result in the fluid or most of the fluid flowing into the bypass conduit 346 from the diverging conduit 310. This fluid flows from the diverging conduit 310 into the lateral bypass conduit 338 via the outlet 316 and the inlet 336. As shown by arrows 404 representing fluid flow in FIG. 4, the fluid flows into the lateral conduit 320 and then into the vertical conduit 322 in the plunger valve 214. The fluid then flows out of the vertical conduit 322 back into the valve housing 200 (e.g., into the vertical bypass conduit 340) while the plunger valve 214 continues to be pressed downward as shown in FIG. 4. The fluid flows into the primary flow conduit 306 in the valve housing 200 and out of the valve housing 200 into the downstream line 110 via the outlet 204 of the housing 200. The fluid is then delivered into the downstream line 110 to fill or otherwise prime the downstream line 110. Bypassing the check valve 304 in this bypass or actuated state of the valve assembly 102 can allow for the downstream line 110 to be filled or otherwise primed much faster (e.g., more than twice as fast or more than ten times as fast) than filling or priming the downstream line 110 using gravity or an infusion pump (e.g., as the pump 112). The conduits 346, 338, 320, 322 through which the fluid flows in the actuated state can be referred to as bypass conduits.

One the downstream line 110 is filled or primed, the operator or user can change the state of the valve assembly 102 to the default or non-actuated state by releasing the contact head 216 of the plunger valve 214. This state of the valve assembly 102 is shown in FIG. 5. The release of pressure onto the plunger valve 214 can cause the plunger valve 214 to move within the interior chamber 300 of the valve housing 200 away from the bottom interior surface 342 of the valve housing 200. For example, the flexible head 216 of the plunger valve 214 may lift the bottom portion of the plunger valve 214 away from the bottom interior surface 342 of the valve housing 200, as shown in FIG. 5.

As the plunger valve 214 moves upward, the lateral inlet 324 of the plunger valve 214 is no longer lined up with or fluidly coupled with the lateral bypass conduit 338 of the valve housing 200. As a result, the fluid in the diverging conduit 310 of the cap plate 210 can no longer flow into the lateral inlet 324 of the plunger valve 214 via the bypass conduit 346 of the cap plate 210 and the lateral conduit 338 of the valve housing 200. Instead, the fluid flows from the diverging conduit 310 into the flow-through conduit 314 of the cap plate 210, and then into the check valve 304 (as represented by arrows 500). As shown in FIG. 5, some fluid may move around and through the check valve 304. The check valve 304 can permit the fluid to flow only toward the downstream line 110 to prevent backflow of fluid from the downstream line 110 to the upstream line 106.

The fluid flows through the check valve 304 and into the primary flow conduit 306 in the valve housing 200 and out of the valve housing 200 into the downstream line 110 via the outlet 204 of the housing 200. The fluid is then delivered into the downstream line 110 to feed the patient 108 or otherwise deliver the fluid. Because the resistance to flow of the fluid in the conduit 306 may be less than the resistance to upward flow of the fluid in the vertical conduit 340, most or all of the fluid may flow from the check valve 304 to the outlet 204 via the conduit 306. But, some fluid (less than half the fluid in the valve assembly 102) may enter into the space in the interior chamber 300 between the bottom side 316 of the plunger valve 214 and the bottom surface 342 of the interior chamber 300.

Figure 6:
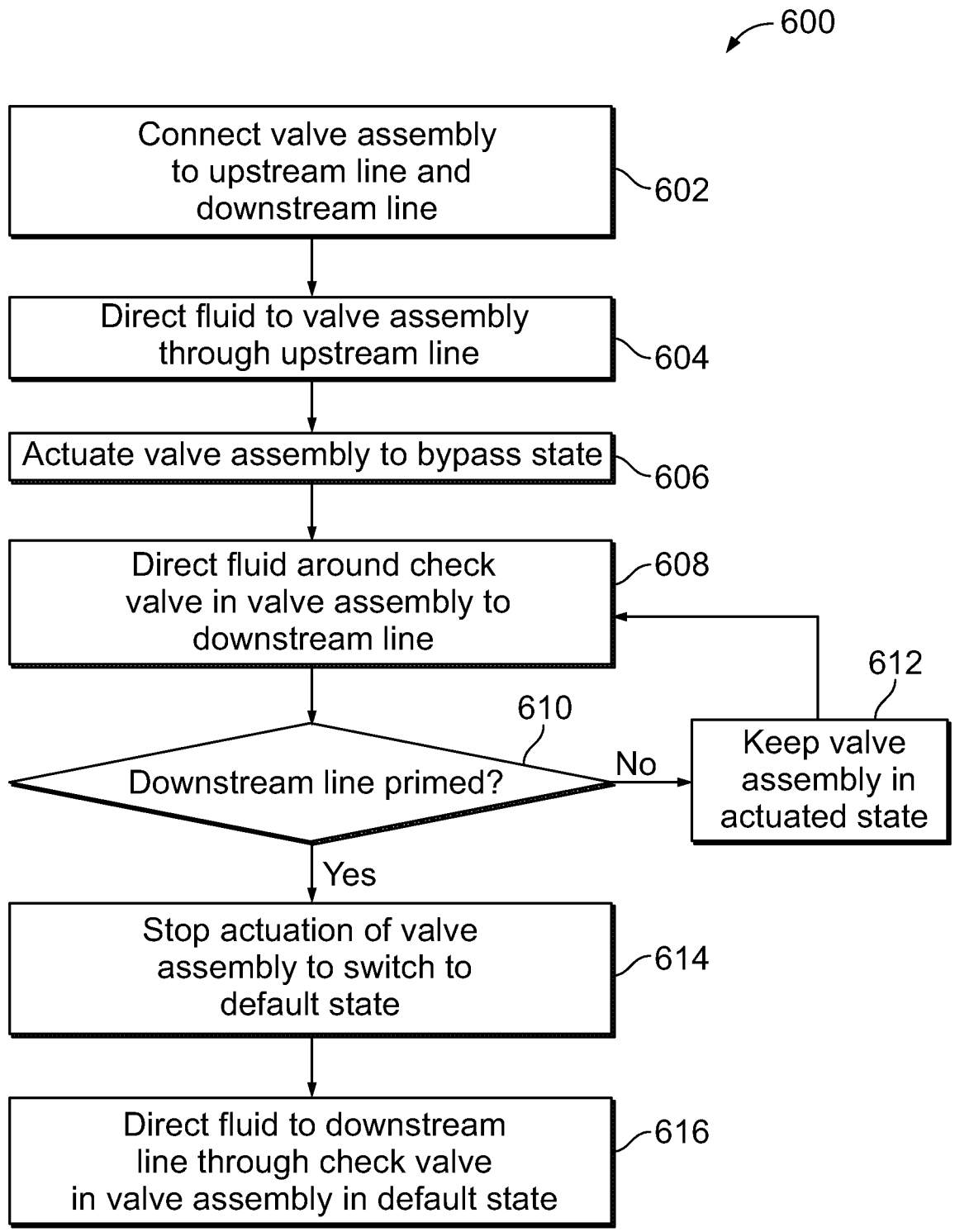
FIG. 6 illustrates a flowchart of one example of a method for controlling flow of fluid using a valve assembly.

FIG. 6 illustrates a flowchart of one example of a method 600 for controlling flow of fluid using a valve assembly. The method 600 can represent one set of operations performed using the valve assembly 102 shown in FIGS. 1 through 5 to control the flow of fluid from the upstream line 106 (shown in FIG. 1) to the downstream line 110 (shown in FIG. 1). At 602, the valve assembly is coupled with the upstream and downstream lines. For example, the upstream line 106 can be coupled with the cap inlet 212 (shown in FIG. 2) and the downstream line 110 can be coupled with the outlet 204 (shown in FIG. 2).

At 604, fluid is directed to the valve assembly through the upstream line. For example, gravity or a pump may force the fluid through the upstream line and into the valve assembly. Alternatively, manual force may be applied (e.g., to a bag) to force the fluid through the upstream line and into the valve assembly. At 606, the valve assembly is actuated to a bypass state. As described herein, the valve assembly may be actuated by pushing down (and maintaining downward force) on the contact head or button 216 (shown in FIG. 2) of the plunger valve 214 (shown in FIG. 2). Also as described above, pushing down on the plunger valve 214 establishes a bypass flow path for the fluid that bypasses the check valve 304 (shown in FIG. 3) of the valve assembly 102.

At 608, fluid is directed around the check valve in the valve assembly to the downstream line. For example, the fluid may pass through conduits in the plunger valve 124 that establish a path around, and not through, the check valve 304. This can permit the fluid to more rapidly flow through the valve assembly 102 to the downstream line 110. At 610, a determination is made as to whether the downstream line is primed with the fluid. For example, a determination may be made as to whether the fluid has filled or substantially filled (e.g., at least 90% filled) the downstream line 110. Alternatively, a determination may be made as to whether the fluid has filled at least a desired amount of the downstream line 110. If the downstream line is primed, then no further fluid may need to be rapidly directed into the downstream line by flowing around, and not through, the check valve in the valve assembly. As a result, flow of the method 600 can proceed toward 614. But, if the downstream line is not primed, then additional fluid may need to be rapidly directed into the downstream line by flowing around, and not through, the check valve in the valve assembly. As a result, flow of the method 600 can proceed toward 612.

At 612, the valve assembly is maintained in the actuated state. For example, the head or button 216 of the plunger valve 214 may remain depressed or held down by an operator or user. Flow of the method 600 can then return toward 608 for additional fluid to be directed around the check valve and to the downstream line via the valve assembly.

At 614, actuation of the valve assembly is terminated. For example, once the downstream line is primed, the operator or user may no longer depress the head or button 216 of the plunger valve 214. This can allow the plunger valve 214 (or at least a bottom half of the plunger valve 214) to move upward in the housing 200 (shown in FIG. 2) of the valve assembly 102. This upward movement can interrupt the flow path that was established in the actuated state to direct the fluid to flow around the check valve. At 616, additional fluid is directed to the downstream line through the check valve in the valve assembly. For example, because the bypass flow path around the check valve in the valve assembly is no longer available, the fluid may be forced to flow through the check valve to the downstream line. In an enteral feeding application, the fluid may flow through the check valve to a patient connected to the downstream line.

In one embodiment, an enteral feeding valve assembly is provided. The valve assembly includes a housing assembly having an inlet configured to be fluidly coupled with an upstream line and an outlet configured to be fluidly coupled with a downstream line. The housing assembly includes a diverging conduit that extends inward from the inlet and a primary conduit that extends inward from the outlet. The diverging conduit splits into a bypass conduit and a flow-through conduit. The flow-through conduit is fluidly coupled with the primary conduit by a check valve. The valve assembly also includes a plunger valve disposed in the housing assembly and configured to move relative to the housing assembly. The plunger valve includes one or more plunger conduits. The plunger valve is configured to be actuated to move in a first direction in the housing assembly to fluidly couple the inlet of the housing assembly with the primary conduit and the outlet of the housing assembly via the bypass conduit of the housing assembly and the one or more plunger conduits of the plunger valve. The plunger valve directs fluid received via the inlet of the housing assembly to the outlet and around the check valve in the housing assembly while the plunger valve is actuated. The plunger valve is configured to move in a different, second direction upon release of the plunger valve to de-couple the inlet of the housing assembly with the primary conduit and the outlet via the bypass conduit of the housing assembly and the one or more plunger conduits of the plunger valve. The flow-through conduit of the housing assembly directs the fluid received via the inlet of the housing assembly to the outlet through the check valve in the housing assembly while the plunger valve is released.

Optionally, the housing assembly includes a cap plate and a housing, the cap plate including the diverging conduit, the bypass conduit, and the flow-through conduits. The housing includes a lateral conduit aligned with and fluidly coupled with the bypass conduit. The housing also includes the primary conduit and a vertical conduit fluidly coupled with the primary conduit.

Optionally, the housing assembly includes an interior chamber in which the plunger valve is disposed, the housing assembly also including a lateral conduit that extends from the bypass conduit to the interior chamber. The housing assembly can include a vertical conduit that extends from the interior chamber to the primary conduit.

Optionally, the plunger valve is configured to move in a downward direction in the interior chamber of the housing assembly as the first direction and is configured to move in an upward direction in the interior chamber of the housing assembly as the second direction.

Optionally, the one or more plunger conduits are aligned and fluidly coupled with the lateral conduit of the housing assembly while the plunger valve is moved in the first direction. The one or more plunger conduits may not be aligned and may not be fluidly coupled with the lateral conduit of the housing assembly while the plunger valve is moved in the second direction.

Optionally, the one or more plunger conduits are spaced apart from the lateral conduit and the vertical conduit of the housing assembly while the plunger valve is not moved in the first direction.

Optionally, the plunger valve is more flexible than the housing assembly.

In one embodiment, a valve assembly is provided that includes a cap plate having an inlet configured to be fluidly coupled with an upstream line. The cap plate includes a diverging conduit that extends inward from the inlet and that splits into a bypass conduit and a flow-through conduit. The valve assembly also includes a rigid housing having an outlet configured to be fluidly coupled with a downstream line. The housing includes a primary conduit that extends inward from the outlet. The primary conduit is fluidly coupled with the flow-through conduit by a check valve. The valve assembly also includes a flexible plunger valve disposed in the housing and configured to move relative to the housing. The plunger valve includes one or more plunger conduits and is configured to be actuated to move in a first direction in the housing to fluidly couple the inlet of the cap plate with the primary conduit and the outlet of the housing via the bypass conduit of the cap plate and the one or more plunger conduits of the plunger valve. The plunger valve directs fluid received via the inlet of the cap plate to the outlet of the housing and around the check valve in the housing assembly while the plunger valve is actuated.

Optionally, the plunger valve is configured to move in a different, second direction upon release of the plunger valve to de-couple the inlet of the cap plate with the primary conduit and the outlet of the housing via the bypass conduit of the housing and the one or more plunger conduits of the plunger valve.

Optionally, the flow-through conduit of the cap plate is shaped to direct the fluid received via the inlet of the cap plate to the outlet through the check valve and the primary conduit in the housing while the plunger valve is released.

Optionally, the housing includes a lateral conduit aligned with and fluidly coupled with the bypass conduit of the cap plate. The housing also can include a vertical conduit fluidly coupled with the primary conduit.

Optionally, the one or more plunger conduits are aligned and fluidly coupled with the lateral conduit of the housing while the plunger valve is moved in the first direction. The one or more plunger conduits may not be aligned and may not be fluidly coupled with the lateral conduit of the housing while the plunger valve is not moved in the first direction.

Optionally, the one or more plunger conduits are spaced apart from the lateral conduit and the vertical conduit of the housing while the plunger valve is not moved in the first direction.

Optionally, the housing includes an interior chamber in which the plunger valve is disposed.

Optionally, the plunger valve is configured to move in a downward direction in the interior chamber of the housing as the first direction.

In one embodiment, a method is provided that includes filling an upstream line coupled with an inlet of an enteral feeding valve assembly with a fluid, and pressing a plunger valve in the valve assembly downward into a housing assembly of the valve assembly. The plunger valve is pressed downward to establish a bypass fluid flow path for the fluid to flow around a check valve in the valve assembly. The method also includes priming a downstream line coupled with an outlet of the valve assembly with the fluid that flows through the bypass fluid flow path and around the check valve in the valve assembly, and releasing the plunger valve to interrupt the bypass fluid flow path and to direct the fluid to flow through the check valve in the valve assembly to the downstream line.

Optionally, the plunger valve includes one or more plunger conduits that are aligned and fluidly coupled with one or more other conduits in the bypass fluid flow path while the plunger valve is pressed downward in the housing assembly.

Optionally, the one or more plunger conduits in the plunger valve are not aligned and not fluidly coupled with the one or more other conduits in the bypass fluid flow path while the plunger valve is not pressed downward in the housing assembly.

Optionally, the downstream line is filled with the fluid more rapidly while the plunger valve is pressed downward in the housing assembly than while the plunger valve is not pressed downward in the housing assembly.

Optionally, the fluid does not flow through the check valve or any other check valve while the plunger valve is pressed downward in the housing assembly.

The singular forms "a", "an", and "the" include plural references unless the context clearly dictates otherwise. "Optional" or "optionally" means that the subsequently described event or circumstance may or may not occur, and that the description may include instances where the event occurs and instances where it does not. Approximating language, as used herein throughout the specification and claims, may be applied to modify any quantitative representation that could permissibly vary without resulting in a change in the basic function to which it may be related. Accordingly, a value modified by a term or terms, such as "about," "substantially," and "approximately," may be not to be limited to the precise value specified. In at least some instances, the approximating language may correspond to the precision of an instrument for measuring the value. Here and throughout the specification and claims, range limitations may be combined and/or interchanged, such ranges may be identified and include all the sub-ranges contained therein unless context or language indicates otherwise.

This written description uses examples to disclose the embodiments, including the best mode, and to enable a person of ordinary skill in the art to practice the embodiments, including making and using any devices or systems and performing any incorporated methods. The claims define the patentable scope of the disclosure, and include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. An enteral feeding valve assembly comprising:
   a housing assembly having an inlet configured to be fluidly coupled with an upstream line and an outlet configured to be fluidly coupled with a downstream line, the housing assembly including a diverging conduit that extends inward from the inlet and a primary conduit that extends inward from the outlet, the diverging conduit splitting into a bypass conduit and a flow-through conduit, the flow-through conduit fluidly coupled with the primary conduit by a check valve; and
   a plunger valve disposed in the housing assembly and configured to move relative to the housing assembly, the plunger valve including one or more plunger conduits,
   the plunger valve configured to be actuated to move in a first direction in the housing assembly to fluidly couple the inlet of the housing assembly with the primary conduit and the outlet of the housing assembly via the bypass conduit of the housing assembly and the one or more plunger conduits of the plunger valve, the plunger valve directing fluid received via the inlet of the housing assembly to the outlet and around the check valve in the housing assembly while the plunger valve is actuated,
   the plunger valve configured to move in a different, second direction upon release of the plunger valve to de-couple the inlet of the housing assembly with the primary conduit and the outlet via the bypass conduit of the housing assembly and the one or more plunger conduits of the plunger valve, the flow-through conduit of the housing assembly directing the fluid received via the inlet of the housing assembly to the outlet through the check valve in the housing assembly while the plunger valve is release,
   the plunger valve is formed from a body that includes the one or more plunger conduits extending through the body, the body of the plunger valve being more flexible than the housing assembly.

2. The enteral feeding valve assembly of claim 1, wherein the housing assembly includes a cap plate and a housing, the cap plate including the diverging conduit, the bypass conduit, and the flow-through conduit, the housing including a lateral conduit aligned with and fluidly coupled with the bypass conduit, the housing also including the primary conduit and a vertical conduit fluidly coupled with the primary conduit.

3. The enteral feeding valve assembly of claim 1, wherein the housing assembly includes an interior chamber in which the plunger valve is disposed, the housing assembly also including a lateral conduit that extends from the bypass conduit to the interior chamber, the housing assembly including a vertical conduit that extends from the interior chamber to the primary conduit, the lateral conduit and the vertical conduit intersecting each other in the housing assembly.

4. The enteral feeding valve assembly of claim 3, wherein the plunger valve is configured to move toward the primary conduit in the interior chamber of the housing assembly as the first direction and is configured to move away from the primary conduit in the interior chamber of the housing assembly as the second direction.

5. The enteral feeding valve assembly of claim 3, wherein the one or more plunger conduits are aligned and fluidly coupled with the lateral conduit of the housing assembly while the plunger valve is moved in the first direction, the one or more plunger conduits not aligned and not fluidly coupled with the lateral conduit of the housing assembly while the plunger valve is moved in the second direction.

6. The enteral feeding valve assembly of claim 3, wherein the one or more plunger conduits are spaced apart from the lateral conduit and the vertical conduit of the housing assembly while the plunger valve is not moved in the first direction.

7. A valve assembly comprising:
   a cap plate having an inlet configured to be fluidly coupled with an upstream line, the cap plate including a diverging conduit that extends inward from the inlet and that splits into a bypass conduit and a flow-through conduit;

a rigid housing having an outlet configured to be fluidly coupled with a downstream line, the housing including a primary conduit that extends inward from the outlet, the primary conduit fluidly coupled with the flow-through conduit by a check valve; and a flexible plunger valve disposed in the housing and configured to move relative to the housing, the plunger valve including one or more plunger conduits, the plunger valve configured to be actuated to move in a first direction in the housing to fluidly couple the inlet of the cap plate with the primary conduit and the outlet of the housing via the bypass conduit of the cap plate and the one or more plunger conduits of the plunger valve, the plunger valve directing fluid received via the inlet of the cap plate to the outlet of the housing and around the check valve in the housing while the plunger valve is actuated.

8. The valve assembly of claim 7, wherein the plunger valve is configured to move in a different, second direction upon release of the plunger valve to de- couple the inlet of the cap plate with the primary conduit and the outlet of the housing via the bypass conduit of the housing and the one or more plunger conduits of the plunger valve.

9. The valve assembly of claim 8, wherein the flow-through conduit of the cap plate is shaped to direct the fluid received via the inlet of the cap plate to the outlet through the check valve and the primary conduit in the housing while the plunger valve is released.

10. The valve assembly of claim 7, wherein the housing includes a lateral conduit aligned with and fluidly coupled with the bypass conduit of the cap plate, the housing also including a vertical conduit fluidly coupled with the primary conduit.

11. The valve assembly of claim 10, wherein the one or more plunger conduits are aligned and fluidly coupled with the lateral conduit of the housing while the plunger valve is moved in the first direction, the one or more plunger conduits not aligned and not fluidly coupled with the lateral conduit of the housing while the plunger valve is not moved in the first direction.

12. The valve assembly of claim 10, wherein the one or more plunger conduits are spaced apart from the lateral conduit and the vertical conduit of the housing while the plunger valve is not moved in the first direction.

13. The valve assembly of claim 7, wherein the housing includes an interior chamber in which the plunger valve is disposed.

14. The valve assembly of claim 13, wherein the plunger valve is configured to move in a downward direction in the interior chamber of the housing as the first direction.

15. A method comprising:

filling an upstream line coupled with an inlet of an enteral feeding valve assembly with a fluid;

pressing a plunger valve in the valve assembly downward into a housing assembly of the valve assembly, the plunger valve having (a) a lateral conduit extending from a first side to an opposite second side of a body of the plunger valve and (b) a vertical conduit that intersects the lateral conduit between the first side and the second side of the body, the vertical conduit extending from the lateral conduit to a plunger outlet on a bottom side of the body, the plunger valve pressed downward to establish a bypass fluid flow path for the fluid to flow around a check valve in the valve assembly via the lateral conduit, the vertical conduit, and the plunger outlet;

priming a downstream line coupled with an outlet of the valve assembly with the fluid that flows through the bypass fluid flow path and around the check valve in the valve assembly; and releasing the plunger valve to interrupt the bypass fluid flow path and to direct the fluid to flow through the check valve in the valve assembly to the downstream line.

16. The method of claim 15, wherein the lateral conduit and the vertical conduit in the body of the plunger valve are not aligned and not fluidly coupled with one or more other conduits in the bypass fluid flow path while the plunger valve is not pressed downward in the housing assembly.

17. The method of claim 15, wherein the downstream line is filled with the fluid more rapidly while the plunger valve is pressed downward in the housing assembly than while the plunger valve is not pressed downward in the housing assembly.

18. The method of claim 15, wherein the fluid does not flow through the check valve or any other check valve while the plunger valve is pressed downward in the housing assembly.

* * * * *